United States Patent [19]

Smestad

[11] 4,430,760

[45] Feb. 14, 1984

[54] NONSTRESS-BEARING IMPLANTABLE BONE PROSTHESIS

[75] Inventor: Thomas L. Smestad, San Jose, Calif.

[73] Assignee: Collagen Corporation, Palo Alto, Calif.

[21] Appl. No.: 332,325

[22] Filed: Dec. 18, 1981

[51] Int. Cl.³ .............................................. A61F 1/00
[52] U.S. Cl. ..................................... 3/1.9; 128/92 G; 128/92 C
[58] Field of Search ............ 128/92 C, 92 G, DIG. 7; 3/1, 1.9, 1.91, 1.4

[56] References Cited

U.S. PATENT DOCUMENTS

| | | | |
|---|---|---|---|
| 2,621,145 | 12/1952 | Sano | 3/1.9 |
| 4,186,448 | 2/1980 | Brekke | 128/92 G |
| 4,277,238 | 7/1981 | Katagiri | 128/92 G |
| 4,298,002 | 11/1981 | Ronel et al. | 604/891 |
| 4,352,883 | 10/1982 | Lim | 3/1 |

FOREIGN PATENT DOCUMENTS 30583  6/1981  European Pat. Off. .............. 3/1.9

*Primary Examiner*—Richard J. Apley
*Assistant Examiner*—D. J. Isabella
*Attorney, Agent, or Firm*—Ciotti & Murashige

[57] ABSTRACT

A flexible, nonstress-bearing bone prosthesis is disclosed that comprises demineralized bone powder contained within a medical grade porous flexible casing made from polymeric fibers or a micro-porous membrane. The pores of the casing are smaller than the particle size of the bone powder but large enough to permit ingress of body cells associated with bone formation.

6 Claims, No Drawings

NONSTRESS-BEARING IMPLANTABLE BONE PROSTHESIS

DESCRIPTION

1. Technical Field

This invention relates to an osteogenic, implantable nonstress-bearing bone prosthesis comprising demineralized bone or dentin powder contained in a flexible porous medical grade casing.

2. Background Art

Demineralized bone in both solid and powder form has been used extensively to repair or replace bone. Once it is implanted, induced osteogenesis occurs at the implant site and bone is formed. Implanted demineralized bone powder, because it is particulate, is more readily and completely invaded by osteogenic cells than solid, one-piece demineralized bone. Because of its nature, however, powder is difficult to form into larger size prostheses of predefined shape. Another problem with implanting bone powder is that it may migrate and induce bone formation at a remote, undesirable site. A prosthesis made from solid cancellous bone may allow cellular invasion throughout the prosthesis because cancellous bone is inherently porous. But cancellous bone prostheses are limited in shape and size to the source bone shape and dimensions. Use of one-piece compact bone for prosthesis construction would allow the manufacture of larger implants. Compact bone is, however, inherently too dense to permit complete cellular invasion and the interior of a large compact bone prosthesis may remain unossified.

U.S. Pat. No. 3,849,805 describes an alloplastic tray that is used as a stress-bearing bone prosthesis, especially for mandibular reconstruction. The tray is made from Dacron or nylon mesh which is dipped in a polyether urethane elastomer and then cured to increase the rigidity of the tray. The patent does not indicate the pore size of the mesh. It is believed that the pore size would have to be greatly in excess of one mm in order to avoid being coated over by the elastomer. The tray contains fresh autologous bone chips.

Buring, K. and Urist, M., Transfilter Bone Induction, Clinical Orthopaedics and Related Research, Vol 54, pp 235–242 (1967) report transfilter bone induction experiments in which millipore membrane diffusion cells intended to be impermeable to host cells were filled with a mixture of minced allogeneic muscle and decalcified, lyophylized bone matrix and implanted in rabbits. Several of the test cells fractured in situ and permitted host connective tissue cells to stream into the cell chamber. Bone induction at the points of contact between the matrix and ingrowing mesenchymal cells was observed.

DISCLOSURE OF THE INVENTION

The invention is a nonstress-bearing implanatable bone prosthesis comprising particulate demineralized bone, dentin, or mixtures thereof contained within a medical grade flexible porous casing, the pores of which are smaller than the particle size of the particulate demineralized bone or dentin, but large enough to permit ingress of osteogenic or mesenchymal cells.

MODES FOR CARRYING OUT THE INVENTION

The bone or dentin that is used in the invention may be collected from a variety of mammalian sources. Homogeneic and xenogeneic sources may be used. The processing of dentin for use in the invention is essentially the same as the processing of bone for use in the invention. Therefore, in the interest of brevity, only the processing of bone will be hereafter described in detail.

The bone may be either cancellous or compact. Bovine and porcine bone, preferably long bone, will normally be used because of its availability. The surface of the bone is first cleaned by physically removing periosteum by scraping or brushing. The bone is then fragmented into small pieces and the fragments are water washed with agitation to remove any water soluble materials remaining on the fragments. The washing is preferably carried out at reduced temperatures that lessen the likelihood of enzymatic degradation of the bone, usually about 4° C. to 15° C., with frequent changing of the wash water. The fragments are then dried, extracted with one or more lipophilic solvents, such as ethanol and ethyl acetate, to remove lipids and dehydrate the bone. The fragments are then dried under vacuum and comminuted by crushing, milling, or pulverizing, preferably at reduced temperatures to increase the friability of the bone. The bone is accordingly converted into a finely divided powder having a particle size in the range of about 40 to 500 microns, preferably 75 to 250 microns. Division of the bone into small particles facilitates extracting the minerals from it.

The principal mineral component of bone is calcium phosphate. The term "calcium phosphate" as used herein is intended to encompass all the calcium-phosphorous complexes and compounds present in bone such as the various polycalcium phosphates, hydroxyapatite, chlorapatite, and the like. Calcium phosphate usually constitutes about 80% by weight of the mineral content of bone. Other mineral components of bone include calcium carbonate, calcium fluoride, calcium chloride, and magnesium phosphate. These minerals are normally soluble in dilute mineral and organic acids and such acids may be used to demineralize bone. The concentration of the acid used to demineralize the bone will usually be between 0.1 M and 1.0 M. Hydrochloric acid at a concentration of 0.5 M is preferred. The bone will normally be contacted with the acid for one hour to several days at reduced temperatures that lessen the likelihood of enzymatic degradation or acid hydrolysis of the bone, typically about 4° C. to about 15° C. Agitation facilitates extraction of the minerals from the bone. After the extraction is complete the bone is separated from the acid such as by sedimentation, filtration or other conventional solid-liquid separation techniques and the bone is washed sequentially with water, ethanol, and ether to remove absorbed acid and dehydrate it. The dried bone may be sterilized by irradiation, ethylene oxide treatment, or other known solids sterilization methods if it is desired to do so before placing it in the casing.

The porous casing in which the demineralized bone or dentin powder is contained is made from a natural or synthetic fibrous or microporous polymer. The casing should be biocompatible that is, it should not be significantly irritating or antigenic. It may be made from polymers that maintain their integrity even after prolonged emplacement in the body or from polymers that bioerode or otherwise disintegrate after a predetermined time period correlated to the time required for the implant to reach a suitable stage of ossification. In the case of fibrous casings, the fabric may be woven or nonwoven. Examples of woven medical grade fabrics are the Dacron and nylon and carbon fabrics that are commonly used in biomedical devices such as stents, prosthetic tendons, and vascular grafts. Examples of suitable nonwoven fabrics are those made of natural materials such as collagen or synthetic materials such as polyesters, polyamides, or polyolefins that are used as fabric backings for wound dressings. Crosslinked collagen is a preferred fabric material.

Microporous polymers that may be used as casings are characterized as having a sponge-like porous nature. These microporous polymers are made by forming pores in various kinds of dense polymers such as polycarbonates, polyamides, polyesters, polyolefins, polysaccharides, and cellulosics by leaching, orientation, or other well-known pore-forming techniques.

The casing may be formed from a single homogeneous layer of one of the above described fibrous or microporous materials or be a laminate of two or more layers of such materials. In any event the casing must be sufficiently porous to permit ingress of host osteogenic and/or mesenchymal cells into the casing lumen but not so porous as to allow the bone or dentin powder contained within the casing lumen to leak out. The maximum pore size will be less than the minimum particle size of the demineralized bone or dentin powder. Accordingly, for embodiments having particle sizes down to 40 microns, the maximum pore size will be below 40 microns. For the abovementioned preferred particle size range the maximum pore size will be less than 75 microns. Correspondingly, the minimum pore size will usually be at least 5 microns. Preferably, it is about 10-15 microns below the minimum particle size of the demineralized bone or dentin powder.

The fabric-encased osteogenic implant may be assembled from the demineralized bone and/or dentin powder and porous casing in several ways. One assembly technique involves forming an open-ended pouch from the fabric or microporous membrane, depositing the powder in the pouch and then sealing the pouch. Sealing may be accomplished by stitching, adhesives, heat and pressure, or other means depending upon the nature of the casing. Another assembly technique involves forming a closed container from the fabric or microporous membrane and then injecting the bone powder in the form of an aqueous slurry through the casing into the container. The injection site may be sealed with a medical grade sealant or cement if necessary. This latter assembly technique would probably be carried out only as part of the surgical operation. The former technique is preferred. The assembly will be made using sterile components and conditions or, in the case of the former assembly method, the implant may be packaged and terminally sterilized using irradiation, ethylene oxide, or other known suitable solids sterilization methods. The pouch or container may, of course, be fashioned into any desired size or shape before being filled to accommodate the optimum prosthesis size and shape. The fine demineralized bone powder gives the implant a high effective surface area which facilitates rapid and complete ossification of the implant. In this regard the demineralized powder ossifies at its surface first. In contrast, bone that has not been demineralized is resorbed first and is then ossified. The porosity of the implant permits bone-forming cell permeation throughout the implant and its flexibility allows the implant to be deformed at the time of implantation to an exact fit of the implant site.

The assemblies are implanted surgically by known methods. If the implant is dry (i.e. it comprises encased dry demineralized bone powder) it should be wetted with sterile physiological saline or the like before it is implanted. If necessary the assembly may be sutured in place to ensure its immobilization. The assembly will preferably include a sewing ring to facilitate such affixation. After implantation, induced osteogenesis occurs, thus forming bone in the shape of the implanted pouch. If desired, bone growth stimulants such as bone morphogenetic protein or those disclosed in U.S. Pat. No. 4,191,747 at col. 3, line 50 to col. 4, line 13, which disclosure is incorporated herein by reference, as well as other agents such as anesthetics, hemostats, antibiotics or other drugs, may be included in the assembly either at the time it is assembled or on implantation by injecting, coating or other means of inclusion.

The implants may be used to replace or repair lost, damaged, or deformed nonstress-bearing bone tissue in living mammals, including humans. In this regard the term "nonstress-bearing" refers to bone tissue that does not normally bear substantial loads, such as craniofacial bone other than the load-bearing parts of the jaw.

Modifications of the above-described modes for carrying out the invention that are obvious to those of ordinary skill in the chemical, surgical, medical, medical device, and related arts are intended to be within the scope of the following claims.

I claim:

1. An implantable nonstress-bearing bone prosthesis comprising particulate demineralized bone, dentin, or mixtures thereof contained within the interior of a medical grade flexible porous closed container made of bioerodible collagen, the pores of which are smaller than the particle size of the particulate demineralized bone or dentin, but large enough to permit passage of osteogenic and/or mesenchymal cells.

2. The implantable nonstress-bearing bone prosthesis of claim 1 wherein the particle size of the particulate demineralized bone or dentin is in the range of about 40 to about 500 microns.

3. The implantable nonstress-bearing bone prosthesis of claim 1 wherein the particle size of the particulate demineralized bone or dentin is in the range of about 75 to 250 microns.

4. The implantable nonstress-bearing bone prosthesis of claim 2 or 3 wherein the size of the pores in the container is about 10-15 microns below the minimum particle size of the demineralized bone.

5. The implantable nonstress-bearing bone prosthesis of claim 1 wherein the container is made from a nonwoven fabric of bioerodible collagen.

6. The implantable nonstress-bearing bone prosthesis of claim 1, 4 or 5 wherein the container is made from crosslinked collagen.

* * * * *